US006124099A

United States Patent [19]
Heckman et al.

[11] Patent Number: 6,124,099
[45] Date of Patent: Sep. 26, 2000

[54] METHOD FOR PLACING A PHOTO-CROSS-LINKING AGENT AT SPECIFIC INTERNAL SITES WITHIN THE SEQUENCE OF SYNTHETIC STRANDS OF RIBONUCLEIC ACIDS

[75] Inventors: Joyce E. Heckman; Robert Pinard; John M. Burke, all of Burlington, Vt.

[73] Assignee: The University of Vermont and State Agricultural College, Burlington, Vt.

[21] Appl. No.: 09/102,599

[22] Filed: Jun. 22, 1998

[51] Int. Cl.$^7$ ...................................................... C12Q 1/68
[52] U.S. Cl. .................................................................. 435/6
[58] Field of Search .............................. 435/6; 536/24.2, 536/26.6

[56] References Cited

U.S. PATENT DOCUMENTS

| | | | |
|---|---|---|---|
| 4,835,263 | 5/1989 | Nguyen et al. | 536/27 |
| 5,219,734 | 6/1993 | Royer et al. | 435/6 |
| 5,292,873 | 3/1994 | Rokita et al. | 514/44 |
| 5,296,350 | 3/1994 | Rokita et al. | 435/6 |
| 5,449,602 | 9/1995 | Royer et al. | 435/6 |
| 5,466,786 | 11/1995 | Buhr et al. | 536/26.26 |
| 5,493,012 | 2/1996 | Rokita et al. | 536/26.6 |
| 5,525,495 | 6/1996 | Keene et al. | 435/172.3 |
| 5,550,039 | 8/1996 | Trachtenberg | 435/1.2 |
| 5,561,222 | 10/1996 | Keene et al. | 530/350 |
| 5,587,361 | 12/1996 | Cook et al. | 514/44 |
| 5,608,046 | 3/1997 | Cook et al. | 536/23.1 |
| 5,623,068 | 4/1997 | Reddy et al. | 536/25.34 |
| 5,670,633 | 9/1997 | Cook et al. | 536/23.1 |
| 5,681,941 | 10/1997 | Cook et al. | 536/23.1 |
| 5,741,643 | 4/1998 | Gryaznov et al. | 435/6 |
| 5,747,253 | 5/1998 | Ecker et al. | 435/6 |
| 5,750,667 | 5/1998 | Wickens et al. | 536/23.1 |

FOREIGN PATENT DOCUMENTS

| | | |
|---|---|---|
| WO94/24120 | 10/1994 | WIPO . |
| WO95/01364 | 1/1995 | WIPO . |

OTHER PUBLICATIONS

Hanna, et al., "Snythesis and characterization. . . ", *Nucl. Acids. Res.*, 1993, 21:9:2073–2079.
Yang, et al., "Specific photocrosslinking of DNA . . . ", *Proc. Natl. Acad.*, 1994, 91:12183–12187.
Harris, et al., "Analysis of the tertiary structure . . . ", *RNA*, 1997, 3:561–576.
Kim, et al., "Site–specific crosslinks of yeast . . . ", *RNA*, 1996, 2:995–1010.
Dontsova, et al., "Three widely separated . . . ", *EMBO J.*, 1992, 11:8:3105–3116.
Rinke–Appel, et al., "The path of mRNA through the *Escherichia coli* . . . ", *EMBO J.*, 1991, 10:8:2195–2202.
Mayer, et al., "Photoaffinity crosslinking of TaqI . . . ", *Gene*, 1995, 153:1–8.
Cassetti, et al., "Interaction of the 82–kDa subunit . . . ", *Proc. Nat. Acad. Sci.*, 1996, 93:7540–7545.
Ikeda, et al., "Characterization of the DNA . . . ", *Biochem & Mol. Bio. Int.*, 1994, 33:3:447–456.
Burgin, et al., "Mapping the active site of . . . ", *EMBO. J.*, 1990, 9:12:4111–4118, Abstract.
Lubini, et al.,"Stabilizing effects of the RNA . . . ", *Chem. Biol.* 1994, 1:1:39–45, Abstract.
Sproat, et al., "2'–O–alkyloligoribonucleotides . . . ", *Nucleic Acids Symp Ser,* 1991, 24:59–62, Abstract.
Lamond, et al., "2'–O–alkyloligoribonucleotides . . . ", *Biochem Soc Trans,* 21:1:1–8, Abstract.
McElhone, et al., "The stability of rat liver . . . ", *Biochem J.* 1971, 125:3:821–827, Abstract.
Gaubatz, et al., "Hybridization of ribosomal RNA . . . ", *Biochemistry,* 1975, 25:14:4:760–765, Abstract.
Irabarren, et al., "2'–O–alkyl oligoribonucleotides . . . ", *Proc Natl Acad Sci,* 1990, 87:19:7747–7751, Abstract.
Beijer, et al., "Snythsis and applications of . . . ", *Nucleic Acids Res,* 1990, 18:17:5143–5151, Abstract.
Johansson, et al., "Target–specific arrest of mRNA . . . ", *Nucleic Acids Res,* 1994, 22:22:4591–4598, Abstract.
Yang, et al., "Specific photocrosslinking of DNA . . . ", *Proc Natl Acad Sci*, 1994, 91:25:12183–12187, Abstract.
Stade, et al., "Site–directed cross–linking of mRNA . . . ", *Nucleic Acids Res*, 1989, 17:23:9889–9908, Abstract.
Columbier, et al al., "Interstrand crosslinking . . . ", *Anti. Nuc. Acid Drug Dev.*, 1997, 7:4:397–402, Abstract.
Cummins, et al., "Characterization of fully . . . ", *Nucleic Acids Res.*, 1995, 23:11:2019–2024, Abstract.
Wang, et al., "Relative stabilities of triple . . . ", *Nucleic Acids Res.*, 1995, 23:7:1157–1164, Abstract.
Wang, et al., "Origins of the large difference . . . ", *Biochemistry,* 1995, 34:12:4125–4132, Abstract.
Leydier, et al., "4'–Thio–RNA: synthesis . . . ", *Antisense Res Dev,* 1995, 5:3:167–174, Abstract.
Lesnik, et al., "Oligodeoxynucleotides containing . . . ", Biochemistry, 1993, 32:30:7832–7838, Abstract.
Shimizu, et al., "Oligo(2'–O–mehtyl)ribonucleotides . . . ", FEBS lett, 1992, 302:2:155–158, Abstract.
Escude, et al., "Stable triple helices are formed . . . ", C R Acad Sci III, 1992, 315:13:521–525, Abstract.
Cotten, et al., "2'O–methyl, 2'–O–ethyl . . . ", Nucleic Acids Res, 1991, 19:10:2629–2635, Abstract.
Zheng, et al., "Characterization of a novel . . . ", Biochemistry, 1998, 37:6:1706–1713, Abstract.
Pinard, R et al., "Site–directed photoaffinity cross–linking., "Gordon Res. Conf.,Nucleic Acids,Jun. 22–24, 1997,and 4th Cambridge Symposium, Oligonucleotide Chemistry and Biology, Aug. 29–Sep. 4, 1997, Abstract.

*Primary Examiner*—Scott W. Houtteman
*Attorney, Agent, or Firm*—Wolf, Greenfield & Sacks, P.C.

[57] ABSTRACT

This invention describes novel photoactive ribonucleotides that contain photocrosslinking agents placed at specific internal positions within a ribonucleotide. The invention also provides methods for identifying novel, sequence-specific target molecules, using the photoactive ribonucleotides of the invention, as well as improved nucleic acid hybridization analysis methods.

20 Claims, No Drawings

METHOD FOR PLACING A PHOTO-CROSS-LINKING AGENT AT SPECIFIC INTERNAL SITES WITHIN THE SEQUENCE OF SYNTHETIC STRANDS OF RIBONUCLEIC ACIDS

GOVERNMENT SUPPORT

The work resulting in this invention was supported in part by NIH Grant No AI30534-08. The U.S. Government may therefore be entitled to certain rights in the invention.

FIELD OF THE INVENTION

This invention relates to photoactive ribonucleotide compounds that can be incorporated into synthetic oligonucleotides during automated synthesis for use in cross-linking of target molecules. The compounds of the invention are used for a variety of diagnostic purposes, such as the identification of sequence-specific RNA-binding target molecules, and detection with increased sensitivity and sequence-specificity of nucleic acid molecules.

BACKGROUND OF THE INVENTION

Specific DNA-protein, DNA-nucleic acid, RNA-protein and RNA-nucleic acid interactions play important roles in the formation of stable structural components of cells, such as transcription complexes, ribosomes and small nuclear ribonucleoprotein particles. Additionally, these interactions are involved in many stages of gene expression and protein synthesis, playing both regulatory and catalytic roles in transcription, RNA processing, splicing, translation and protein targeting. Identification of the specific molecular interactions involved provides insight into the mechanisms of these processes and contributes to a better understanding of the general parameters of molecular recognition involving nucleic acids.

Photochemical cross-linking is a powerful tool for the identification of the specific interactions involved in DNA-protein and DNA-nucleic acid complexes. One approach involves incorporation of nucleotide analogs containing photoreactive cross-linking groups into the DNA. DNA-protein or DNA-nucleic acid complexes are then formed, the complexes are irradiated with ultraviolet (UV) light, and molecules covalently attached to the DNA by photo-cross-linking are identified. The use of such analogs results in much higher DNA cross-linking yields than direct cross-linking by excitation of unmodified nucleic acids. Nucleotide analogs conjugated to photochemical cross-linkers and placed at specific positions within a synthetic DNA molecule have been described in Yang S-W and Nash H. A., *Proc. Natl. Acad. Sci. USA* 1994, 91:12183–12187.

Nucleotide analogs that can be incorporated specifically into the 5'- and/or the 3'-end of RNA molecules also have been described. Such incorporations were achieved enzymatically by RNA polymerases, or chemically with some difficulty. Photo-cross-linking groups have also been placed at specific internal UMP residues in RNA utilizing automated chemical synthesis in a protected phosphoramide precursor. (Bradley, D., and Hanna, M. M., *Tetrahedron Letters* 1992, 33:6223–6226). These modified nucleotides, however, are somewhat labile and they have a very short range of cross-linking, often failing to make a sufficiently close contact with another micromolecule and reacting instead with water. Until recently, placement of photo-cross-linking analogs internally into RNA has been limited to uridine analogs. One of these analogs 5-((4-azidophenacyl) thio)-UTP, which contains a photoreactive azide group approximately 10 Å from the base, is incorporated at internal positions in RNA by both *E. coli* and T7 RNA polymerases without interfering with normal Watson-Crick base pairing (Dissinger, S. and Hanna, M. M., *J. Mol. Biol.* 1991, 219:11–25). Other UDP analogs that are incorporated internally during transcription include 4-thio-UTP, 5-bromo-UTP, and 5 azido-UTP, all of which contain cross-linking groups directly on the nucleotide base and function essentially as 0 Å probes (Woody, A-Y. M., et al., *Biochem. Biophys. Res. Commun.* 1988, 150:917–924).

Aryl azides are chemically inert until irradiated with long wavelength ultraviolet light, when a chemically reactive nitrene is generated on the azide. The nitrene can then insert rapidly and relatively nonspecifically into adjacent molecules, resulting in covalent attachment of the azide-tagged molecule to other molecules in the vicinity. This relatively non-specific insertion reaction makes azides excellent probes for the environment of a molecule, as one specific functional group need not be present on an adjacent molecule to the cross-linking. Using photo-cross-linking, proteins that specifically bind to nucleic acids can be identified, or conformational changes that occur in nucleic acid binding proteins upon interaction with other molecules can be detected.

In spite of the progress made in methodology, a number of problems have prevented the wide scale use of hybridization as a tool in human diagnostics. Among the more formidable problems are: i) the inefficiency of hybridization, and ii) the low concentration of specific target sequences in a mixture of genomic DNA.

SUMMARY OF THE INVENTION

We describe herein novel photoactive ribonucleotides that contain photo-crosslinking agents placed at specific internal positions within a ribonucleotide. The invention also provides methods for identifying novel, sequence-specific target molecules, using the photoactive ribonucleotides of the invention, as well as improved nucleic acid hybridization analysis methods.

There exists a need for synthetic ribonucleic acid molecules that contain a photo-cross-linking agent at any desired internal position within the molecule with a long range of cross-linking that allow a sufficiently close contact of the ribonucleic acid molecule with another micromolecule.

There also exists a need for simplified organic chemical synthesis methods for synthetic ribonucleic acid molecules that contain a photo-cross-linking agent at any desired internal position. There exists a need for easily manipulated synthetic oligonucleotides. There also exists a need for improved hybridization techniques.

According to one aspect of the invention, a method for attaching an energy-inducible crosslinking agent to an internal nucleotide of a synthetic nucleic acid molecule is provided. The energy-inducible crosslinking agent is preferably a photo-crosslinking agent and the crosslinking occurs by applying energy preferably in the form of irradiation. The method involves providing a nucleic acid intermediate having a 3'-terminal ribonucleotide with a protected 2'-OH group, replacing a non-bridging oxygen of a phosphodiester group of the 3'-terminal ribonucleotide with a sulfur group, attaching an extending nucleotide to a bridging oxygen of the phosphodiester group of the 3'-terminal ribonucleotide to form a nucleic acid molecule with an internal sulfur group, and attaching the energy-inducible crosslinking agent to the sulfur group to produce a synthetic nucleic acid-photo-crosslinker conjugate. Preferably, attaching the energy-inducible crosslinking agent to the sulfur group to produce a synthetic nucleic acid-photo-crosslinker conjugate occurs after attaching an extending nucleotide to a bridging oxygen of the phosphodiester group of the 3'-terminal ribonucleotide to form a nucleic acid molecule with an internal sulfur group. In certain embodiments the energy-inducible crosslinking agent is a photo-crosslinking agent selected from the group consisting of p-azidophenacyl bromide, N-[(2-pyridyldithio)ethyl]-4-azidosalicylamide, N-hydroxysuccinimidyl-4-azido-benzoate (HSAB), N-succinimidyl-6 (-4'-azido-2'-nitrophenylamino) hexanoate (SANPAH), succinimidyl 4-[4-bromomethyl-3-nitrobenzoyl]aminobutyrate, succinimidyl 6-[4-bromomethyl-3-nitrobenzoyl] aminohexanoate, and succinimidyl 4-bromomethyl-3-nitrobenzoate. In a preferred embodiment the photo-crosslinking agent is an aryl-azide.

According to another aspect of the invention, a method for capturing a sequence-specific target molecule is also provided. The method involves contacting a synthetic nucleic acid molecule having an energy-inducible crosslinking agent attached to an internal ribonucleotide through a phosphodiester group of ific internal ribonucleotide of the synthetic nucleic acid molecule with a sequence-specific target molecule under conditions that allow binding, and applying irradiation to crosslink the sequence-specific target molecule to the synthetic ribonucleic acid through the energy-inducible crosslinking agent to form a conjugate. The energy-inducible crosslinking agent is preferably a photo-crosslinking agent and the crosslinking occurs by applying energy preferably in the form of irradiation. In certain embodiments, the conjugate is allowed to to form a complex with at least one secondary molecule that interacts with the target molecule. In certain other embodiments, the sequence-specific target molecule is a nucleic acid molecule or a polypeptide molecule and the at least one secondary molecule is a polypeptide molecule.

According to a further aspect of the invention, an improved method for analyzing nucleic acids is provided, wherein the presence or identity of a nucleic acid molecule is determined by hybridizing the nucleic acid molecule to a probe having a complementary sequence to the nucleic acid. The improvement comprises hybridizing to the nucleic acid molecule an oligonucleotide probe having at least one internal nucleotide having the structure:

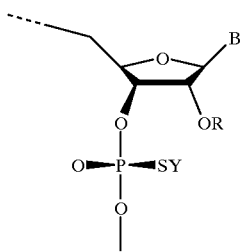

wherein B is a purine or pyrimidine base, R is a protecting moiety and Y is an energy-inducible crosslinking agent, to produce a nucleic acid molecule-oligonucleotide probe complex, and detecting the presence of the complex. The energy-inducible crosslinking agent is preferably a photo-crosslinking agent and the crosslinking occurs by applying energy preferably in the form of irradiation. In some embodiments, the protecting moiety R in the internal ribonucleotide is selected from the group consisting of t-butyldiphenylsilyl, t-butyldimethylsilyl, dimethoxytrityl groups, C1–C12 straight-chained or branched, substituted or unsubstituted alkyl, alkenyl, alkynyl, alkanoyl, aryl, aralkyl, and alkaryl groups. In preferred embodiments the protecting moiety R is a methyl group. In certain embodiments the complex is detected by a southern blot analysis, a northern blot analysis, ribonuclease mapping, or in situ hybridization analysis.

According to another aspect of the invention, an oligonucleotide which contains at least one internal nucleotide having the structure:

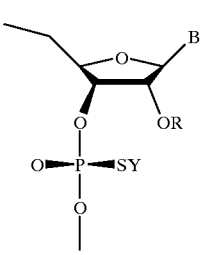

wherein, B is a purine or pyrimidine base, R is a protecting moiety and Y is a photo-crosslinking agent, is provided. In some embodiments, the protecting moiety R in the internal ribonucleotide is selected from the group consisting of t-butyldiphenylsilyl, t-butyldimethylsilyl, dimethoxytrityl groups, C1–C12 straight-chained or branched, substituted or unsubstituted alkyl, alkenyl, alkynyl, alkanoyl, aryl, aralkyl, or alkaryl groups. In other embodiments, the photo-crosslinking agent is selected from the group consisting of p-azidophenacyl bromide, N-[(2-pyridyldithio)ethyl]-4-azidosalicylamide, N-hydroxysuccinimidyl-4-azido-benzoate (HSAB), N-succinimidyl-6 (-4'-azido-2'-nitrophenylamino) hexanoate (SANPAH), succinimidyl 4-[4-bromomethyl-3-nitrobenzoyl]aminobutyrate, succinimidyl 6-[4-bromomethyl-3-nitrobenzoyl]aminohexanoate, and succinimidyl 4-bromomethyl-3-nitrobenzoate. In preferred embodiments the protecting moiety R is a methyl group and the the photo-crosslinking agent is an aryl-azide. In certain other embodiments a labeling molecule is incorporated into the oligonucleotide of the invention. In some embodiments the labeling molecule is selected from the group consisting of biotin, digoxygenin UTP, and a radioactive compound.

In yet another aspect of the invention, a nucleic acid is provided comprising a polymer of nucleotides selected from the group consisting of ZP and Z'P'-SY, wherein ZP is a ribonucleotide or modified ribonucleotide, P is a 3'-phosphodiester group of the ribonucleotide or modified ribonucleotide, Z' is a modified ribonucleotide, P' is a modified 3'-phosphodiester group of the modified ribonucleotide, modified to include a sulfur atom, S is the sulfur group, and Y is an energy-inducible crosslinking agent. The energy-inducible crosslinking agent is preferably a photo-crosslinking agent and the crosslinking occurs by applying energy preferably in the form of irradiation.

The present invention thus involves, in several aspects, photoactive ribonucleotides that contain photo-crosslinking agents placed at specific internal positions within the ribonucleotide, and methods for identifying novel, sequence-specific target molecules using the photoactive ribonucleotides.

These and other objects of the invention will be described in further detail in connection with the detailed description of the invention.

DETAILED DESCRIPTION OF THE INVENTION

One aspect of the invention relates to a method for attaching a photo-cross-linking agent to a specific internal ribonucleotide of a synthetic nucleic acid molecule. As used herein, the term "synthetic nucleic acid" molecule refers to a chemically synthesized "oligonucleotide" molecule, modified or not. A preferred chemical synthesis method according to the invention is one that is automated and involves solid-state support synthetic schemes, although other schemes such as enzymatic methods could also be used.

The term "oligoribonucleotide" refers to a plurality of monophosphate ribonucleotide monomers that are typically formed from naturally occurring bases and ribopentofuranosyl (ribose) sugars joined by native phosphodiester bonds through bridging oxygen atoms in a specific sequence. A "bridging oxygen" atom in a phosphodiester bond of an oligonucleotide is therefore an oxygen atom which joins phosphorous to a sugar. Preferred ribonucleotide monomers for oligomeric compounds of the invention include naturally occurring or synthetic purine or pyrimidine heterocyclic bases, including but not limited to adenine, guanine, cytosine, uracil and inosine. Other representative heterocyclic bases are disclosed in U.S. Pat. No. 3,687,808 (Merigan, et al.), which is incorporated herein by reference. In some embodiments described below the ribonucleotide monomer is a modified ribonucleotide. Thus, "oligoribonucleotide," as used herein, means naturally occuring ribonucleotidesand modified ribonucleotides.

Generally, oligonucleotides of the invention can be of any size but preferably they range from about 3 nucleotides to about 100 nucleotides.

According to the invention, the ribonucleotide monomer to which a photo-crosslinking agent is to be attached is an internal ribonucleotide. By "internal" it is meant that the ribonucleotide is not a 5'- or 3'-end terminal ribonucleotide. The synthetic nucleic acid may include more than one photo-crosslinking agent attached to different internal ribonucleotide monomers. In fact a photo-crosslinking agent may even be attached to a 5'- or 3'-end terminal ribonucleotide as long as one internal ribonucleotide also includes a photo-crosslinking agent attached to it.

The crosslinking agent is attached to the internal ribonucleotide through a sulfur group. Native ribonucleotides do not include a sulfur group. Therefore, the ribonucleotide which will be attached to the crosslinking agent according to the methods of the invention must be chemically manipulated to incorporate a sulfur group.

The sulfur group replaces one or more non-bridging oxygen atoms of the phosphodiester group of the specific internal ribonucleotide to form a phosphorothioate ribonucleotide. The sulfur group can be added to the non-bridging oxygen using methods known in the art. For instance, sulfurization of RNA oligonucleotides during automated chemical synthesis can be performed using 3H-1,2-benzodithiole-3-1,1,1-dioxide (Glen Research Corp., Sterling, Va.) after the coupling step and before the capping step (and according to manufacturer's protocols). As used herein a "non-bridging" oxygen is an oxygen atom which is part of the phosphate group but which does not share a bond with the sugar (ribose) group. Each phosphorothioate ribonucleotide can exist as either an $R_p$ or $S_p$ diastereomer and has the following formula I:

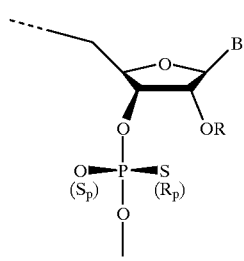

wherein:
B is a purine or pyrimidine base, and
R of OR is a protecting moiety.

It was found according to the invention, that when a sulfur atom is attached to an internal naturally occuring ribonucleotide, then the molecule becomes destabilized and tends to form a cyclic structure between the sulfur and the 2' OH group. In order to prevent the molecular destabilization, the 2'-OH group of the ribonucleotide monomer's ribose is protected using a protecting moiety. A ribonucleotide having a protecting moiety is referred to as a "modified ribonucleotide." "Modified ribonucleotide" monomers used in the synthesis of oligonucleotides according to the present invention can be either purchased directly from the manufacturer (e.g., Glen Research Corp., Sterling, Va.), or protected with a protecting moiety before attaching a photo-crosslinking agent to a specific internal ribonucleotide of a synthetic ribonucleic acid molecule. "Protecting groups" typically are known per se as chemical functional groups that can be selectively appended to and removed from functionalities, such as hydroxyl groups and carboxyl groups. These groups are present in a chemical compound to render such functionality inert to chemical reaction conditions to which the compound is exposed. For example, in the context of the present invention, the 2'-OH group of the ribose after modification with a "Protecting group" becomes resistant to crosslinking with the highly reactive sulfur group that is subsequently added to a non-bridging oxygen of the phosphodiester group of the ribonucleotide and before the addition of a photo-crosslinking agent. In the present invention, however, it is not necessary to "deprotect" the molecule to recreate the native 2'-OH. Instead, the protecting moiety can be essentially a hydrogen replacing moiety, substituting a less reactive R group for the hydrogen. In preferred embodiments, the molecule is deprotected.

Numerous suitable protecting moieties can be used to replace the hydrogen of the 2'-OH functional group of the compounds of the invention during synthesis. Such groups include but are not limited to t-butyldiphenylsilyl, t-butyldimethylsilyl, dimethoxytrityl groups, C1–C12 straight-chain or branched alkyl, alkenyl, alkynyl, alkanoyl, aryl, aralkyl, or alkaryl groups.

As used in this specification, "alkyl" groups of the invention include but are not limited to C1–C12 straight- and branched-chain alkyls such as methyl, ethyl, propyl, butyl, pentyl, hexyl, heptyl, octyl, nonyl, decyl, undecyl, dodecyl, isopropyl, 2-butyl, isobutyl, 2-methylbutyl, isopentyl, 2-methylpentyl, 3-methylpentyl, 2-ethylhexyl and 2-propylpentyl. Alkenyl groups include but are not limited to unsaturated moieties derived from the above alkyl groups including but not limited to vinyl, allyl and crotyl. Alkynyl groups include unsaturated moieties having at least one triple bond that are derived from the above alkyl groups including but are not limited to ethynyl and propargyl. Alkanoyl groups according to the invention are alkyl, alkenyl or alkynyl groups attached through a carbonyl group.

The term "aryl" is intended to denote monocyclic and polycyclic aromatic groups including, for example, phenyl, naphthyl, xylyl, pyrrole, and furyl groups. Although aryl groups (e.g., imidazo groups) can include as few as 3 carbon atoms, preferred aryl groups have 6 to about 12 carbon atoms, more preferably 6 to about 10 carbon atoms. Aralkyl and alkaryl groups according to the invention each include alkyl and aryl portions. Aralkyl groups are attached through their alkyl portions, and alkaryl groups are attached through their aryl portions. Benzyl groups provide one example of an aralkyl group, and p-tolyl provides an example of an alkaryl group.

The terms alkyl, alkaryl, aralkyl and aryl are intended to denote both substituted (e.g., halogenated and hydroxylated) and unsubstituted moieties. Substitutions can occur by one or several halogen, cyano, amino, carboxy, ester, ether and carboxamide groups (see, e.g., Veber and Hirschmann, et al., *J. Org. Chem.* 1977, 42:3286 and Atherton, et al., *The Peptides*, Gross and Meienhofer, Eds, Academic Press; New York, 1983; Vol. 9:1–38). Other representative protecting groups suitable for practice in the invention may be found in Greene, T. W. and Wuts, P. G. M., *"Protective Groups in Organic Synthesis"* 2d. Ed., Wiley & Sons, 1991. Although each protecting moiety described above may be used, a methyl group is a preferred such moiety according to the invention.

As described above, the photo-crosslinking agent is attached to the ribonucleotide through the sulfur group. The phosphorothioate ribonucleotide of formula I either as a monomer, or as part of a synthetic oligonucleotide of the invention, is a universal acceptor for a variety of agents, including photo-crosslinking agents, so long as the agent has, or is attached to, a thiol-reactive moiety. In general the thiol-reactive photo-crosslinking agent is attached to the sulfur group by chemical methods known in the art (Hixson, S. H. and Hixson, S. S. *Biochemistry* 1975, 14:4251; Hanna, M. M. and Meares, C. F., *J Am. Chem. Soc.* 1983, 22:3546–3551; Burgin, A. B. and Pace, N. R., *EMBO J.* 1990, 9:4111–4118—all of which are incorporated herein by reference). For instance, a thiol-reactive photo-crosslinking agent can be coupled (attached) to a phosphothioate group of an oligonucleotide by incubating at room temperature for 1 hour 100 nmol of the sulfur-containing-oligonucleotide in 20 ml of 20 mM sodium bicarbonate (pH 9.0) containing 45% (vol/vol) dimethyl sulfoxide and 5.0 mM thiol-reactive photo-crosslinking agent (e.g., azidophenacyl bromide, Fluka). The excess photo-crosslinking agent is typically washed-off using isobutyl alcohol washes.

Generally, "crosslinking agents" are moieties that can effect intrastrand or interstrand covalent binding of RNA and/or DNA, and include photo-crosslinking agents. A "photo-crosslinking agent" as used herein, is a thiol-reactive compound which can form covalent bonds with a proximate compound when exposed to irradiation. Photo-crosslinking agents are well known in the art. The photo-crosslinking agents useful according to the invention may have thiol-reactive groups or may be modified by routine chemical procedures to incorporate a thiol-reactive group. In certain embodiments, photo-crosslinking agents include, and are not limited to, azides. Photo-crosslinking of azide-bearing nucleotides or nucleic acids to associated proteins is thought to proceed via formation of the singlet and/or triplet nitrene (Bayley and Knowles, *Methods Enzymol.* 1977, 46:69; Czarnecki et al., *Methods Enzymol.* 1979, 56:642; Hanna et al., *Nucleic Acids Res.* 1993, 21:2073). Covalent bond formation results from insertion of the nitrene in an O—H, N—H, S—H or C—H bond. Singlet nitrenes preferentially insert in heteroatom-H bonds and triplet nitrenes in C—H bonds. Singlet nitrenes can also rearrange to azirines which are prone to nucleophilic addition reactions. If a nucleophilic site of a protein is adjacent, crosslinking can also occur via this pathway.

Examples of "photo-crosslinking agents" of the invention include but are not limited to aryl azides such as p-azidophenacyl bromide, N-[(2-pyridyldithio)ethyl]-4-azidosalicylamide, N-hydroxysuccinimidyl-4-azidobenzoate (HSAB) and N-succinimidyl-6(-4'-azido-2'-nitrophenylamino) hexanoate (SANPAH). Other useful photo-crosslinking agents include succinimidyl 4-[4-bromomethyl-3-nitrobenzoyl]aminobutyrate, succinimidyl 6-[4-bromomethyl-3-nitrobenz]aminohexanoate, and succinimidyl 4-bromomethyl-3-nitrobenzoate. More representative photo-crosslinking agents are disclosed in International Patent Application Ser. No. PCT/US93/02059, which is incorporated herein by reference. Although the specific choice in selecting a photo-crosslinking agent will be apparent to one of ordinary skilled in the art, p-azidophenacyl bromide is a preferred agent according to the invention. One advantage to the compounds of the invention is that photo-crosslinking agents attached (via covalent bonding) to oligonucleotides of this invention, can be stored in the dark long-term because of the stability of the bonds formed after attachment of the photo-crosslinking agent to the oligonucleotide.

Photo-crosslinking agents attached to oligonucleotides of the invention crosslink with a target molecule which is in close proximity with the oligonucleotide upon irradiation. As used herein, "irradiation" refers to subjecting the synthetic ribonucleic acid-photo-cross-linker/nucleic acid or polypeptide conjugate to light, preferably ultraviolet (UV) light, which causes conversion of the azide group of the photo-crosslinking agent to a nitrene compound. The nitrene inserts into the bonds of the target molecule, causing the target molecule to remain in close proximity to the oligonucleotide. The preferred UV wavelength is $\geq 300$ nm, and in a preferred embodiment the UV wavelength used for crosslinking is 312 nm.

In certain embodiments, in addition to the photo-crosslinking agent a labeling molecule may be incorporated into the oligonucleotide of the invention or the target molecule in a manner which will allow for detection and/or isolation of a conjugate/complex formation. A wide variety of "labeling molecules" may be used, and one or another labeling molecule may be selected depending upon the desired sensitivity, the equipment available for measuring, the particular protocols employed, ease of synthesis, and the like. Such "labeling molecules" include enzymes, fluorescers, chemilluminescers, radionuclides, enzyme substrates, cofactors or suicide inhibitors, specific binding members, particularly haptens or the like. The labeling molecule involved with detection may be covalently bound to the oligonucleotide. Alternatively, it may be indirectly bound through an intermediary molecule, for example, a short probe (nucleic acid or protein which specifically interacts with a sequence of the oligonucleotide) covalently bound to a label attached to a region of the oligonucleotide remote the specific internal ribonucleotide, or may be indirectly bound through the intermediary molecule of a specific binding pair, i.e., ligand and receptor. Examples of ligands and receptors include biotin-avidin, hapten-antibody, ligand-surface membrane receptor, metal-chelate, etc.

According to the invention, a novel method for capturing a sequence-specific target molecule is provided. The method includes contacting under conditions favorable for binding a synthetic nucleic acid molecule of the invention (an oligonucleotide having a photo-crosslinking agent attached to an internal ribonucleotide) with a sequence-specific target molecule. As used herein, a "sequence-specific target molecule" is a molecule that recognizes a specific sequence of nucleotides and binds covalently to such sequence. These "sequence-specific target molecules" are involved in many stages of gene expression and protein synthesis, playing both regulatory and catalytic roles in transcription, RNA processing, splicing, translation and protein targeting. Examples of such molecules are nucleic acids and proteins. Other specific examples include, but are not limited to, ribosomes and small nuclear ribonucleoprotein particles. In certain embodiments, a labeling molecule as described in the preceding paragraph may also be incorporated into the synthetic ribonucleic acid molecule in order to facilitate the isolation and characterization of such novel RNA sequence-specific target molecules.

After allowing for the recognition and binding of an oligonucleotide of the invention to a sequence-specific target molecule, UV irradiation is applied to cross-link the sequence-specific target molecule to the synthetic ribonucleic acid through the photo-crosslinking agent to form a conjugate of the ribonucleic acid and the target molecule. Such conjugates can then be isolated and characterized using procedures well known to those of ordinary skill in the art (see also the Examples). For instance, the crosslinked conjugate can be separated from the other components in the incubation mixture by chromatography. This is followed by digestion of the purified complex with a protease and isolation of the peptide that remains covalently joined to the nucleic acid molecule. The amino-terminal sequence of this peptide indicates which portion of the protein is near the derivatized residues on the nucleic acid molecule, and the point of interruption of the peptide sequence can provide clues as to the actual amino acids involved in the linkage.

In some embodiments, the conjugate is allowed to form a complex with at least one secondary molecule that interacts with the target molecule. A "secondary molecule" as used herein is a molecule which recognizes and binds to the oligonucleotide-target molecule complex or the target molecule. The secondary molecules can also be isolated and characterized using methods identical to the methods used for the identification of the target molecules. In certain embodiments the sequence-specific target molecule and the secondary molecule are selected from the group consisting of a polypeptide molecule, a peptide-nucleic acid molecule and a nucleic acid molecule. Preferably, at least one secondary molecule is a polypeptide molecule.

As used herein, the term "polypeptide molecule" is used to describe naturally occurring or synthetic compounds ranging from about 1 to about 1000 amino acid residues covalently linked by peptide bonds, and thus includes peptides, polypeptides, and proteins. Preferably, the amino acids are naturally occurring amino acids in the L-configuration. The polypeptide, for example, may be an RNA and/or DNA binding factor, an enzyme, a substrate, a ligand for a receptor, a cytokine, a cofactor, or an antibody.

The invention also provides an improved method for analyzing nucleic acids and has numerous advantages over existing methods. The improvement involves using an oligonucleotide probe having at least one internal nucleotide having the structure of formula II:

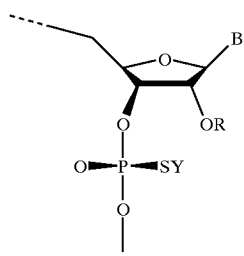

wherein, B is a purine or pyrimidine base, R is a protecting moiety, and Y is a photo-crosslinking agent.

The identity of a nucleic acid can be determined by methods well known in the art, such as Northern blot analysis, Southern blot analysis, ribonuclease mapping, in situ hybridization and other methods whose experimental details are described in, for example, Sambrook, J. et al., 1989, *Molecular Cloning*, Cold Spring Harbor Laboratory Press. In general, these methods involve hybridizing a probe having a complementary sequence to the nucleic acid to determine whether the particular nucleic acid is present in a sample. The identification of the nucleic acid in these methods is dependent on the interaction between the nucleic acid and the probe. If the interaction is a weak interaction then the specificity of the method is compromised. The methods of the invention offer improvements to these prior art methods. When the oligonucleotide probe set forth above is used as a probe to identify a nucleic acid, the strength of the probe-nucleic acid interaction is increased because the crosslinker stabilizes the interaction.

In one embodiment, the oligonucleotide probe is a labeled nucleic acid of defined base sequence and is capable of hybridizing with a nucleic acid having a complementary sequence. By "labeled" it is meant that a labeling molecule, as described earlier, is also incorporated into the oligonucleotide. The complementary sequence is referred to as the target sequence. The nucleic acids may include native, recombinant, or synthetic target sequences. These include, but are not limited to genomic DNA, cDNA, mRNA and RNA. By "hybridizing" it is meant that the labeled oligonucleotide probe is first allowed to non-covalently interact through hydrogen bonding, salt bridges, and/or Van der Waal forces with the target sequence in accordance with standard hybridization techniques (see e.g. Sambrook, J. et al., 1989, *Molecular Cloning*, Cold Spring Harbor Laboratory Press), and is subsequently covalently cross-linked, preferably using UV irradiation. As a result, the sensitivity of the hybridization assay is increased, allowing for stronger and specific probe/target interactions.

According to the invention, a nucleic acid is provided comprising a polymer of nucleotides selected from the group consisting of ZP and Z'P'-SY monomers. Thus, for illustration purposes, the following polymer (pentamer) is provided:

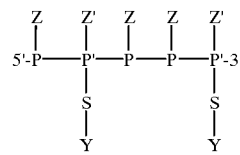

wherein at least one internal Z'P'-SY is present. ZP is a ribonucleotide or modified ribonucleotide; P is a 3'-phosphodiester group of the ribonucleotide or modified ribonucleotide, Z' is a modified ribonucleotide, P' is a modified 3'-phosphodiester group of the modified ribonucleotide, modified to include a sulfur atom, S is the sulfur group, and Y is an energy-inducible crosslinking agent. The energy-inducible crosslinking agent is preferably a photo-crosslinking agent and the crosslinking occurs by applying energy preferably in the form of irradiation. As described earlier, a "modified ribonucleotide" is a ribonucleotide having a protecting moiety.

It is to be understood that while the invention has been described in conjunction with the preferred embodiments thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLES

Experimental Procedures

Synthesis of Oligoribonucleotides

RNA oligonucleotides are synthesized using solid-phase phosphoramidite chemistry performed on an Applied Biosystems, Inc. (Foster City, Calif.) model 392. RNA phosphoramidites and 2'-O-methyl ribonucleotide phosphoramidites can be purchased from Glen Research Corp., Sterling, Va. The sulfuirization of RNA oligonucleotides was carried out during their automated synthesis using 3H-1,2-benzodithiole-3-1,1,1-dioxide after the coupling step and before the capping step. Protecting with the preferred 2'-O-methyl groups are inserted during the RNA oligonucleotide synthesis using the phosphoramidite chemistry, if necessary (2'-OH modified bases can be purchased, for example, from Glen Research Corp., Sterling, Va.). All RNA oligonucleotides used are deprotected by the method of Wincott et al. (*Nuc. Acid. Res.* 1995, 23:2677–2684). Briefly, in deprotection of the synthetic RNA oligonucleotides the synthesis column is removed, and the resin-support is placed into a screw cap Eppendorf tube. The resin-support is first incubated in 1 $\mu$l of concentrated ammonium hydroxide/ethanol, 3:1, at 65° C. for 4 hours. After chilling on ice, the supernatant solution is removed from the resin-support with a sterile pipette into a disposable 14 ml sterile plastic snap-cap top tube. The resin-support is then rinsed twice with 1 ml of sterile water and added to the 14 ml tube. After checking the sample concentration by measuring the $OD_{260}$, the sample is frozen at −70° C. and then freeze-dried overnight in a lyophilizer. A solution of triethylamine trihydrofluoride (Aldrich, 34,464-8) is used to resuspend the lyophilized sample (10 $\mu$l per $OD_{260}$). The sample is vortexed thoroughly and transferred again into a sterile plastic snap-cap top tube. The mixture is left to resuspend for between 20 to 24 hours. The reaction is then quenched with sterile distilled water (2 $\mu$l per $OD_{260}$). To this solution, 1-butanol (Aldrich, 27,067-9) at 100 $\mu$l per $OD_{260}$ is added. The solution is mixed and cooled down to −20° C. or lower for approximately 45 minutes. The tube is spun in a tabletop centrifuge for 5 minutes and the butanol is gently decanted from the RNA pellet. The butanol is completely dried-off under vacuum and the synthetic RNA is dissolved in approximately 100 $\mu$l distilled water and purified using denaturing polyacrylamide gel electrophoresis in TBE buffers, eluted by diffusion, precipitated with ethanol and purified using C8-reverse phase HPLC.

Preparation of Photoagent-Containing Oligonucleotides

Between 10 to 50 $\mu$M of sulfur-containing oligonucleotide are dissolved in 40% methanol, 20 mM sodium bicarbonate pH 9.0, 0.1% sodium dodecyl sulfate (SDS) and 100 mM of the preferred photo-crosslinking agent, p-azidophenacyl bromide, and incubated at room temperature for 3 hours in the dark. Excess photo-crosslinking agent is extracted by centrifugation through a Centricep column (Princeton Separation, Adelphia, N.J.). The photoagent-containing oligonucleotides are separated and isolated by HPLC using a C8 column. After HPLC, the oligonucleotides are extracted three times with 1 volume ether to eliminate traces of acetonitrile and to impair decoupling of the crosslinking photo-agent, are lyophilized, and resuspended in water.

Crosslink Formation

Assembly and crosslinking reactions are typically performed in 50 mM trace-HCl pH 7.5, 12 mM $MgCl_2$. The sequence-specific target molecule (e.g., 3-piece hairpin ribozyme, polypeptide, etc.) is assembled by preincubating the azidophenacyl-containing oligonucleotide with the appropriate fragment(s) or polypeptides in presence of non-cleavable substrate (100 nM) for 15 minutes at 37° C. in the reaction buffer. Solutions are allowed to equilibrate for 10 minutes at room temperature. The assembled complexes are exposed to 312 nm ultraviolet (UV) light (handheld, Model VL-6M, IBI, Inc., New Haven, Conn.) at 40 mm screen by polystyrene filter for 30 minutes at room temperature. The crosslinking conjugates are resolved on a 20% polyacrylamide-7M Urea gel. The cross-linked conjugates are isolated and eluted overnight in elution buffer (0.5M ammonium acetate, 1 mM EDTA, 0.1% SDS, precipitated and passed through a Centrisep column to remove salts.

Reaction mixtures like those described above can be scaled-up in order to obtain enough of the conjugated molecules.

Example 1

Polypeptide-Nucleic Acid Crosslinked Conjugates Experimental Strategy

When a sequence specific target molecule binds to nucleic acid, it usually protects a region that encompasses between 10 and 30 nucleotides. Moreover, the affinity with which the sequence specific target molecule binds a synthetic oligonucleotide is close to that for binding to a much larger nucleic acid fragment. Accordingly, crosslinking probes can be conveniently made by (i) chemically synthesizing an oligomer in which one or more specific backbone phosphodiesters are replaced by phosphorothioate; and (ii) mixing this oligonucleotide with a photo-crosslinking agent. Optionally, a labeling agent can also be incorporated into the oligonucleotide (e.g., radioactive agent, Biotin, Digoxygenin, etc.). The derivatized nucleic acid is then allowed to interact with the sequence specific target molecule in a solution by incubation, and the solution is then irradiated.

In choosing which positions of the nucleic acid molecule to derivatize, one of ordinary skill in the art could be guided by the pattern of conservation of bases among the sequence specific target molecule recognition sites. Rather than relying on a single site of derivatization, one can synthesize a synthetic nucleic acid in which two or more adjacent phosphodiester positions are replaced by phosphorothiote.

The crosslinked conjugate can be separated from the other components in the incubation mixture by chromatography. This is followed by digestion of the purified complex with a protease and isolation of the peptide that remains covalently joined to the nucleic acid molecule. The amino terminal sequence of this peptide indicates which portion of the protein is near the derivatized residues on the nucleic acid molecule, and the point of interruption of the peptide sequence can provide clues as to the actual amino acids involved in the linkage. The following sections describe in more detail the specific steps of the methods and certain embodiments of the invention.

Peptide Sequence of the Crosslinked Conjugate

The purified crosslinked conjugate is heated at 60° C. for 10 minutes to denature the protein and chilled on ice for 10 minutes. After incubation at 37° C. for 5 minutes, modified trypsin (2 μg; Promega, Madison, Wis.) and 2 μl of 100 mM calcium chloride are added. The mixture is incubated at 37° C. for 2 hours and for another 1 hour at room temperature. The resulting peptide-nucleic acid conjugate is ethanol precipitated and subjected to 2M Urea/12% PAGE in 0.5×TBE. The resulting band containing the peptide-nucleic acid conjugate is localized, for example, by autoradiography, excised, and passively eluted overnight with 1 ml of 50 mM trace-HCl (pH 8.0) containing 1 mM EDTA. The eluate is passed through a gel filtration column (PD-10, Pharmacia) and equilibrated with HPLC-grade water. The amount of crosslinked peptide-nucleic acid conjugate is then estimated by measuring the $OD_{260}$. The eluate is dried completely and peptide sequences in the material are identified by automated Edman degradation (Edman, P. N. and Begg, G., *Eur. J. Biochem.* 1967, 1:80–91).

Example 2

Site-directed Photoaffinity Crosslinking in a Novel Construct of the Hairpin Ribozyme Crosslink Formation Assembly and crosslinking reactions are performed as described above in Example 1. The 3-piece hairpin ribozyme is assembled by preincubating the azidophenacyl-containing oligonucleotide with the appropriate fragment(s) in presence of non-cleavable substrate (100 nM) for 15 minutes at 37° C. in the reaction buffer. In each set of reaction, one of the strands of the hairpin ribozyme can be 5'-$^{32}$P-end labeled. Solutions are allowed to equilibrate for 10 minutes at room temperature. The assembled complexes are exposed to 312 nm ultraviolet (UV) light (handheld, Model VL-6M, IBI, Inc., New Haven, Conn.) at 40 mm screen by polystyrene filter for 30 minutes at room temperature. The crosslinking conjugates are resolved on a 20% polyacrylamide-7M Urea gel. The cross-linked conjugates are isolated and eluted overnight in elution buffer (0.5M ammonium acetate, 1 mM EDTA, 0.1% SDS, precipitated and passed through a Centrisep column to remove salts.

Mapping of the Crosslinked Species

The conjugated sites of the gel-purified cross-linked species are determined by partial digestions using Rnases $T_1$ and $U_2$ and limited alkaline hydrolysis using manufacturer's instructions (Boehringer Manheim, Ind.). Samples are then loaded onto a 20% denaturing polyacrylamide gel. Non-cross-linked 5'-$^{32}$P-end labeled RNA is digested by Rnases $T_1$ and $U_2$ and subjected to identical limited alkaline hydrolysis to serve as markers in identifying the conjugated sites.

Equivalents

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

We claim:

1. A method for attaching a photo-crosslinking agent to an internal nucleotide of a synthetic nucleic acid molecule comprising:

(a) providing a nucleic acid intermediate having a 3'-terminal ribonucleotide with a protected 2'-OH group, (b) replacing a non-bridging oxygen of a phosphodiester group of the 3'-terminal ribonucleotide with a sulfur group, (c) attaching an extending nucleotide to a bridging oxygen of the phosphodiester group of the 3'-terminal ribonucleotide to form a nucleic acid molecule with an internal sulfur group, and (d) attaching the photo-crosslinking agent to the sulfur group to produce a synthetic nucleic acid-photo-crosslinker conjugate.

2. The method of claim 1, wherein the photo-crosslinking agent is selected from the group consisting of p-azidophenacyl bromide, N-[(2-pyridyldithio)ethyl]-4-azidosalicylamide, N-hydroxysuccinimidyl-4-azidobenzoate (HSAB), N-succinimidyl-6 (-4'-azido-2'-nitrophenylamino)hexanoate(SANPAH), succinimidyl 4-[4-bromomethyl-3-nitrobenzoyl]aminobutyrate, succinimidyl 6-[4-bromomethyl-3-nitrobenzoyl]aminohexanoate, and succinimidyl 4-bromomethyl-3-nitrobenzoate.

3. A method for capturing a sequence-specific target molecule comprising:

(a) contacting a sequence-specific target molecule with a synthetic nucleic acid molecule having a photo-crosslinking agent attached to an internal ribonucleotide of the synthetic nucleic acid molecule through a phosphodiester group of the internal ribonucleotide, and (b) applying irradiation to crosslink the sequence-specific target molecule to the synthetic ribonucleic acid through the photo-crosslinking agent to form a conjugate.

4. The method of claim 3, further comprising:

producing a complex by allowing the conjugate to form a complex with at least one secondary molecule that interacts with the target molecule.

5. The method of claim 4, wherein the sequence-specific target molecule is a nucleic acid molecule and the at least one secondary molecule is a polypeptide molecule.

6. The method of claim 4, wherein the sequence-specific target molecule is a polypeptide molecule and the at least one secondary molecule is also a polypeptide molecule.

7. An improved method for analyzing nucleic acids wherein the presence or identity of a nucleic acid molecule is determined by hybridizing the nucleic acid molecule to a probe having a complementary sequence to the nucleic acid molecule, the improvement comprising:

hybridizing to the nucleic acid molecule an oligonucleotide probe having at least one internal nucleotide having the structure:

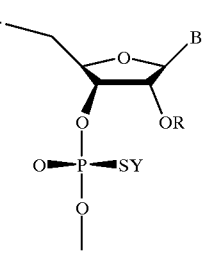

wherein:
B is a purine or pyrimidine base;
R is a protecting moiety;
Y is a photo-crosslinking agent, to produce a nucleic acid molecule-oligonucleotide probe complex, and detecting the presence of the complex.

8. The method of claim 7, wherein the protecting moiety R is selected from the group consisting of t-butyldiphenylsilyl, t-butyldimethylsilyl, dimethoxytrityl groups, C1–C12 straight-chained or branched, substituted or unsubstituted alkyl, alkenyl, alkynyl, alkanoyl, aryl, aralkyl, or alkaryl groups.

9. The method of claim 7, wherein the protecting moiety R is a $CH_3$ group.

10. The method of claim 7, wherein the complex is detected by a southern blot analysis.

11. The method of claim 7, wherein the complex is detected by a northern blot analysis.

12. The method of claim 7, wherein the complex is detected by ribonuclease mapping.

13. The method of claim 7, wherein the complex is detected by in situ hybridization analysis.

14. An oligonucleotide which contains at least one internal nucleotide having the structure:

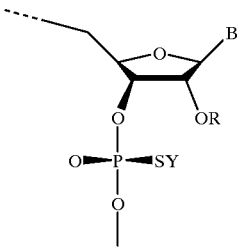

wherein:

B is a purine or pyrimidine base;

R is a protecting moiety;

Y is a photo-crosslinking agent.

15. The oligonucleotide of claim 14, wherein the protecting moiety R is selected from the group consisting of t-butyldiphenylsilyl, t-butyldimethylsilyl, dimethoxytrityl groups, C1–C12 straight-chained or branched, substituted or unsubstituted alkyl, alkenyl, alkynyl, alkanoyl, aryl, aralkyl, and alkaryl groups.

16. The oligonucleotide of claim 14, wherein the protecting moiety R is a $CH_3$ group.

17. The oligonucleotide of claim 14, wherein the photo-crosslinking agent is selected from the group consisting of p-azidophenacyl bromide, N-[(2-pyridyldithio)ethyl]-4-azidosalicylamide, N-hydroxysuccinimidyl-4-azidobenzoate(HSAB), N-succinimidyl-6 (-4'-azido-2'-nitrophenylamino)hexanoate(SANPAH), succinimidyl 4-[4-bromomethyl-3-nitrobenzoyl]aminobutyrate, succinimidyl 6-[4-bromomethyl-3-nitrobenzoyl]aminohexanoate, and succinimidyl 4-bromomethyl-3-nitrobenzoate.

18. The oligonucleotide of claim 14, further comprising a labeling molecule attached to the oligonucleotide.

19. The oligonucleotide of claim 18, wherein the labeling molecule is selected from the group consisting of biotin, digoxygenin UTP, and a radioactive compound.

20. A nucleic acid comprising a polymer of nucleotides selected from the group consisting of ZP and Z'P'-SY, wherein at least one internal Z'P'-SY is present, and wherein ZP is a ribonucleotide or modified ribonucleotide, P is a 3'-phosphodiester group of the ribonucleotide or modified ribonucleotide, Z' is a modified ribonucleotide, P' is a modified 3'-phosphodiester group of the modified ribonucleotide, modified to include a sulfur atom, S is the sulfur group, and Y is a photo-crosslinking agent.

* * * * *